United States Patent [19]

van Venrooy

[11] 4,093,647
[45] June 6, 1978

[54] PROCESS FOR OXYCARBONYLATION OF AROMATIC HYDROCARBONS

[75] Inventor: John J. van Venrooy, Media, Pa.

[73] Assignee: Suntech, Inc., Wayne, Pa.

[21] Appl. No.: 826,291

[22] Filed: Aug. 22, 1977

[51] Int. Cl.² .............................................. C07C 63/00
[52] U.S. Cl. ................................................ 260/515 R
[58] Field of Search ..................................... 260/515 R

[56] References Cited

U.S. PATENT DOCUMENTS

| | | | |
|---|---|---|---|
| 3,579,552 | 5/1971 | Craddock et al. ............... | 260/515 R |
| 3,917,670 | 11/1975 | Baird et al. ....................... | 260/515 R |
| 3,923,883 | 12/1975 | Gaenzler .......................... | 260/515 R |
| 3,952,034 | 4/1976 | Thompson et al. ............. | 260/515 R |

*Primary Examiner*—A. Siegel
*Attorney, Agent, or Firm*—J. Edward Hess; Donald R. Johnson; Paul Lipsitz

[57] ABSTRACT

A process for making aromatic carboxylic acids by reacting carbon monoxide with an aromatic compound in the presence of a mixture of a thallium salt and a palladium salt whereby highly efficient use of the available oxidant is achieved.

8 Claims, No Drawings

PROCESS FOR OXYCARBONYLATION OF AROMATIC HYDROCARBONS

Oxycarbonylation reactions, whereby carbon monoxide is introduced into an organic moiety to obtain a carboxylic acid, are known in the art. An early reference to such reactions is L. Barlow and J. Davidson, Chem. and Ind., 1965, p. 1656 which describes the reaction of phenylmercurinitrate with CO in benzene solution at high pressure (about 250 atm.) to yield benzoic acid.

Later, P. Henry, (Tetrahedron Letters 19, 2285 (1968)) combined various arylmercuric compounds with $PdCl_2$ in solution and obtained increased yields of carboxylic acids under ambient pressure and temperature.

It has now been found that oxycarbonylation of an uncondensed aromatic hydrocarbon to an aromatic carboxylic acid can be achieved with high efficiency by use of a mixture comprising salts of palladium and thallium. In addition, the process of the invention yields predominantly the highly desired para isomer when the starting aromatic compound is alkyl substituted. Thus, with toluene as starting hydrocarbon, the product toluic acid contains a high proportion of p-toluic acid which is the most useful isomer.

The process of the invention is applicable to a aromatic hydrocarbons of the benzene series having at least one hydrogen atom attached to an aromatic carbon atom. The process is inoperable with condensed ring systems such as naphthalene. Aromatic hydrocarbons of the benzene series and its lower alkyl substituted derivatives are typically useful.

The mixture of inorganic salts is made up of a major amount of the thallium salt and a minor amount of the expensive palladium salt. The molar ratio of thallium to palladium may vary from about 10 to 1 to as much as 1000 to 1 but preferably in the range of 100 to 1. The thallium salt should be in the trivalent state and comprise trifluoroacetate anions. Thus $Tl(OOCCF_3)$ is a required thallium salt. The palladium salt should be in the divalent state and will contain anions such as halide, acetate, sulfate, oxalate, and the like to aid in solubilizing the material to be treated with CO. The palladium salt of a strong anionic resin (such as Amberlyst X15) may also be used. Palladium chloride is a preferred halide for use in the process.

The reaction will be carried out in an excess of aromatic hydrocarbon reactant and will employ a solvent medium. Examples of useful solvents will include lower (e.g. one to four atoms) aliphatic carboxylic acid (acetic acid, trifluoroacetic acid, butyric acid, etc.), and the corresponding aliphatic acid anhydrides which are liquid under the reaction conditions, (acetic acid anhydride, trifluoroacetic anhydride etc.) and the like. Preferably a mixture of trifluoroacetic acid and trifluoroacetic anhydride will be used in the practice of this invention. Solvents such as carbon tetrachloride and methylcyanide are not useful in the process.

The reaction operating parameters are readily achieved. A reaction temperature range of from about 0° C to about 100° C is useful but 25° C to 50° C is preferred. A carbon monoxide pressure of 10 to 500 psi may be used with 60 to 100 psi preferred.

The reaction requires that both the thallium and palladium salts as well as the aromatic hydrocarbon be present. While the exact mechanism of the reaction is not known it is believed that the thallium forms a complex with the aromatic compound and that transmetallation between thallium and palladium occurs which is followed by insertion of CO into the aromatic C—Pd bond. Nevertheless, it has also been found as indicated above that aromatic hydrocarbon must be present for the uptake of CO to occur. The reason for this is not known, but Example 3 illustrates this phenomenon. Decomposition of the aromatic-palladium complex leads to reduction of the palladium from Pd(II) to Pd(0). Tl(III) reoxidizes Pd(0) back to Pd(II) leading in turn to the formation of Tl(I). The palladium is turned over many times until the supply of the primary oxidant Tl(III) is exhausted. At this point finely dispersed Pd(0) black is formed and carbon monoxide adsorption stops. A small amount of palladium is sufficient therefore to produce a very large amount of the aromatic carboxylic acid.

In order to further illustrate the invention the following examples are given:

EXAMPLE 1

A 75 ml. Fischer-Porter tube was charged with 0.0144 gms of $Pd(OOCCH_3)_2$, 2.5 gms of $Tl(OOCCF_3)_3$, 5.0 ml of trifluoroacetic anhydride, 5.0 ml of trifluoroacetic acid and 15 ml of toluene. The reaction mixture was stirred at room temperature forming a cloudy, tan colored slurry. The reaction mixture was pressured to 96 psig with carbon monoxide. Adsorption of CO was rapid resulting in a drop pressure of 20 psig. CO pressure was maintained by repressuring from 76 to 100 psig. The reaction solution became clear and turned pale yellow in color. The solution finally turned from pale yellow to nearly black in appearance due to the presence of a finely dispersed black solid (reduced palladium). At this point CO adsorption stopped. The contents of the Fischer-Porter tube were poured into 200 ml of water and the basicity of the solution adjusted to pH 10 with sodium hydroxide. The solution was warmed on the steam bath to strip off unreacted toluene and then filtered to remove the black solid. The filtrate was acidified with HCl to pH 2. Upon reaching pH 3 a white precipitate had already begun to come out. This precipitate was found to be a mixture of TlCl and toluic acid. The toluic acid was separated by extraction with diethyl ether and recovered by evaporation of the ether. The recovered toluic acid amounted to 0.5126 gms. Based on the amount of Tl(III) being reduced to Tl(I) this amounts to an 82% utilization of the available oxidant. The toluic acid was analyzed for isomer distribution by conversion to the methyl ester for vapor phase chromatographic analysis. The para isomer amounted to 90.9% along with 4.0% ortho and 5.1% meta. The quantity of Tl(III) is the limiting reagent while toluene is in large excess. The molar ratio of thallium to palladium in this experiment was 72.

EXAMPLE 2

The experiment described in Example 1 was repeated except that the temperature of the reaction mixture was maintained at 0° C. The rate of reaction of the lower temperature was slower so that 30 minutes was required to complete the uptake of CO. Utilization of the Tl(III) oxidant amounted to 78%. The para isomer of toluic acid amounted to 93.8% along with 0.7% ortho and 5.5% meta.

EXAMPLE 3

A quantity of p-tolylthallium bis(trifluoroacetate)

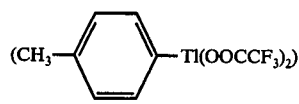

was prepared by the method of A McKillop and J. D. Hunt as reported in J. Organometallic Chemistry, 24 (1970) 77-88. A 75 ml Fischer-Porter tube was charged with 0.0188 gms of Pd(OOCCH$_3$)$_2$, 2.6 gms of p-tolyl thallium bis(trifluoroacetate), 5 ml of trifluoroacetic acid, and 5 ml of trifluoroacetic anhydride. The reaction mixture was stirred at room temperature under 100 psig of CO pressure. Very little CO uptake was observed until 15 ml of toluene was added to the Fisher-Porter tube after which the run proceeded as in Example 1. The recovered toluic acid amounted to 0.2794 gms. Based on the amount of Tl(III) capable of being reduced to Tl(I) this yield amounts to a 45.2% utilization of the available oxidant. The recovered toluic acid product was found to be 85.2% para, 8.5% ortho and 6.3% meta isomer.

EXAMPLE 4

A 75 ml Fisher-Porter tube was charged with 2.5 gms of p-tolyl thallium bis(trifluoroacetate), 10 ml of toluene, 5 ml of trifluoroacetic acid and 5 ml of trifluoroacetic anhydride. The reaction mixture was stirred at room temperature under 84 psig of CO pressure. There was no appreciable uptake of CO nor could any toluic acid be isolated from the reaction product after the workup procedure of Example 1.

EXAMPLE 5

Example 4 was repeated with the exception that the reaction mixture was heated to 80° C for 4 hours. There was no appreciable uptake of CO nor was toluic acid found in the reaction product.

Thus it is seen that the reaction requires the combination of thallium and palladium in order to be operative.

EXAMPLE 6

A 75 ml Fischer-Porter tube was charged with 2.5 gms of Tl(OOCCF$_3$)$_3$, 15 ml. of toluene, 5 ml of acetic anhydride and 2.5 gms of Amberlyst X-15 resin previously exchanged with palladium to the extent of 0.5 wt percent. The reaction mixture was pressured to 100 psig with CO and maintained at room temperature. After the usual work up procedure 0.0842 gms of toluic acid were recovered indicating a 13.5% utilization of the available Tl(III) oxidant. The product contained 95.1% para, 2.9% meta and 2.0 ortho isomers.

EXAMPLE 7

A 75 ml Fischer-Porter tube was charged with 0.0152 gms of Pd(OOCCH$_3$)$_2$, 2.5 gms of TL(OOCCF$_3$)$_3$ 0.5 gms of toluene, 5 ml of trifluoroacetic acid and 5 ml of trifluoroacetic anhydride. The reaction mixture was pressured to 100 psig with CO and maintained at room temperature. The reaction mixture turned a milky beige in color and there was essentially no CO uptake. An additional 0.5 gms of toluene was added to the reaction mixture. CO uptake began and the mixture rapidly turned clear and pale yellow in color and the reaction proceeded as in Example 1. After the usual workup procedure 0.436 gms of toluic acid were recovered indicating a 69.8% utilization of the available Tl(III) oxidant. Conversion of toluene to toluic acid amounted to 29.4%. The product contained 93.0%. The product contained 93.0% para, 3.3% ortho and 3.7% meta isomers.

EXAMPLE 8

The experiment described in Example 1 was repeated except that benzene was used instead of toluene. Benzoic acid was recovered in the amount of 0.5067 gms. This represents a 90% utilization of the available Tl(III) oxidant.

EXAMPLE 9

The experiment described in Example 1 was repeated except that 0.0019 gms of Pd(OOCCH$_3$)$_2$ was used. The rate of reaction was slower so that several hours were required to complete the uptake of CO. Utilization of the Tl(III) oxidant amounted to 92%. The para isomer of toluic acid amounted to 88.0% along with 4.3% ortho and 7.7% meta. The molar ratio of thallium to palladium in this experiment was 550 to 1.

EXAMPLE 11

The experiment described in Example 1 was repeated except that 0.0117 gms of PdCl$_2$ was used along with 0.866 gms of toluene. The recovered toluic acid amounted to 0.471 gms. The isomer distribution was found to be 91.1% para, 4.5% ortho and 4.3% meta.

The invention claimed is:

1. A process for making aromatic carboxylic acids which comprises reacting at a temperature of from about 0° to about 100° C, an aromatic hydrocarbon of the benzene series having at least one ring carbon atom attached to a hydrogen atom with carbon monoxide at a pressure of from about 10 to about 500 psi in a solvent selected from the group consisting of lower aliphatic carboxylic acids, their anhydrides and mixtures thereof and in the presence of a mixture comprising thallium trifluoroacetate and a divalent palladium salt in a mole ratio of thallium to palladium of from about 10:1 to about 1000:1.

2. The process of claim 1 wherein the aromatic compound is toluene.

3. The process of claim 1 wherein the aromatic compound is benzene.

4. The process of claim 1 wherein the aliphatic acid solvent is trifluoroacetic acid.

5. The process of claim 1 wherein the aliphatic acid anhydride is trifluoroacetic anhydride.

6. The process of claim 1 wherein the solvent system comprises a mixture of trifluoroacetic acid and trifluoroacetic acid anhydride.

7. The process of claim 6 wherein the aromatic compound is benzene.

8. The process of claim 6 wherein the aromatic compound is toluene.

* * * * *